United States Patent [19]
Pietrzkowski et al.

[11] Patent Number: 6,017,898
[45] Date of Patent: Jan. 25, 2000

[54] INHIBITION OF TUMOR GROWTH BY ANTISENSE OLIGONUCLEOTIDES FOR IL-8 AND IL-8 RECEPTOR

[75] Inventors: Zbigniew Pietrzkowski, Foothill Ranch; Dariusz Cieslak, Laguna Niguel; Gordana Olbina, San Diego, all of Calif.

[73] Assignee: ICN Pharmaceuticals, Inc., Costa Mesa, Calif.

[21] Appl. No.: 09/055,913

[22] Filed: Apr. 6, 1998

Related U.S. Application Data

[60] Division of application No. 08/796,031, Feb. 5, 1997, Pat. No. 5,849,903, which is a continuation-in-part of application No. 08/561,302, Nov. 21, 1995, abandoned.

[51] Int. Cl.[7] ............................. A61K 48/00; C07H 21/04
[52] U.S. Cl. ................. 514/44; 435/6; 435/375; 435/377; 536/24.1; 536/24.5
[58] Field of Search .................. 435/6, 172.3, 375, 435/377; 514/44; 536/24.5, 24.1

[56] References Cited

PUBLICATIONS

Branch "A Good Antisense Molecule is Hard to Find" TIBS vol. 23: 45–50, 1998.
Agrawal "Antisense Oligonucleotides: Towards Clinical Trials." TIBTECH vol. 14: 376–387, 1996.

*Primary Examiner*—George C. Elliott
*Assistant Examiner*—Sean R. McGarry
*Attorney, Agent, or Firm*—Robert D. Fish; Crockett & Fish

[57] ABSTRACT

Oligonucleotides are provided which are effective in inhibiting the growth, metastasis and/or angiogenesis of tumors, including particularly melanoma and/or lung cancer. Methods are also provided for use of these oligonucleotides in the treatment of diseases.

2 Claims, 4 Drawing Sheets

Fig.1 Growth inhibitory effect of ICN Oligonucleotides for IL-8 at 0.1uM concentration during 72 hrs treatment of Lung, Melanoma, Prostate and Breast Cancer. The results are presented as % of Growth.

FIG.3

Kinetic of Subcutaneous Melanoma Growth in Balb/c Nude/Nude Mice
Expressed as Slope Following Linear Regression Analysis UNPAIRED t-TEST

| Parameter: | UNTREATED | ICN 131 | ICN 70 |
|---|---|---|---|
| Mean: | 3.34 | 2.63 | -0.81 |
| No. of Mice: | 8 | 8 | 8 |
| Std. Dev.: | 1.61 | 1.13 | 1.11 |
| Std. Error: | 0.57 | 0.40 | 0.39 |
| Minimum: | 1.55 | 0.94 | -2.03 |
| Maximum: | 5.87 | 4.15 | 1.27 |
| Median: | 1.99 | 1.68 | -0.92 |

UNT vs ICN 131
$p=0.3280$

UNT vs ICN 70
$p<0.0001$

FIG.4

Kinetic of Subcutaneous Lung Cancer Growth in Balb/c Nude/Nude Mice Expressed as Slope Following Linear Regression Analysis UNPAIRED t-TEST

| Parameter: | UNTREATED | ICN 131 | ICN 70 |
|---|---|---|---|
| Mean: | 26.41 | 16.96 | 12.84 |
| No. of Mice: | 5 | 5 | 5 |
| Std. Dev.: | 8.36 | 7.63 | 6.77 |
| Std. Error: | 3.85 | 3.41 | 3.02 |
| Minimum: | 16.10 | 9.08 | 6.90 |
| Maximum: | 38.00 | 26.98 | 24.04 |
| Median: | 22.96 | 16.11 | 12.37 |

UNT vs ICN 131
$p=0.1039$

UNT vs ICN 70
$p=0.0245$

INHIBITION OF TUMOR GROWTH BY ANTISENSE OLIGONUCLEOTIDES FOR IL-8 AND IL-8 RECEPTOR

This application is a divisional of application Ser. No. 08/796,031 filed Feb. 5, 1997, now U.S. Pat. No. 5,849,903 which is a CIP of application Ser. No. 08/561,302 filed Nov. 21, 1995 (abandoned).

I. FIELD OF THE INVENTION

The field of the invention is oligonucleotide therapeutics, and more particularly the use of oligonucleotides to modulate the expression of IL-8 and/or IL-8 Receptor to control growth, metastasis and/or angiogenesis in tumors.

II. BACKGROUND OF THE INVENTION IL-8

Interleukin-8 (IL-8, neutrophil activating protein-1, or NAP-1) is a member of C-X-C chemokine family of related cytokines having broad involvement in inflammatory responses, tissue injury, growth regulation and cellular adhesion. Cerretti, D. P., et al., Molecular Characterization of Receptors for Human Interleukin-8, GRO/Melanoma Growth-Stimulatory Activity and Neutrophil Activating Peptide-2, *Molecular Immunology*, 30(4), 359–367 (1993); and Koch, A. E., et al., In situ expression of cytokines and cellular adhesion molecules in the skin of patients with systemic sclerosis, *Pathobiology*, 61(5–6), 239–46 (1993). A review of the C-X-C family is given in Streiker, R. M., et al., Role of C-X-C Chemokines As Regulators Of Angiogenesis In Lung Cancer, *J. of Leukocyte Biology*, 57, 752–762 (1995). IL-8 has also been shown to have a potent stimulatory effect on angiogenesis. See, e.g., Koch, A. E., Interleukin-8 as a Macrophage-Derived Mediator of Angiogenesis, *Science*, 258, 1798–1800 (1992).

It is known that IL-8 is produced by a variety of normal human somatic cells including monocytes/macrophages, dermal fibroblasts, vascular endothelial cells, keratinocytes, and mesangeal cells. Yasumoto, K., et al., Tumor Necrosis Factor Alpha and Interferon Gamma Synergistically Induce Interleukin 8 Production in a Human Gastric Cancer Cell Line Though Acting Concurrently on AP-1 and NF-kB-like Binding Sites of the Interleukin 8 Gene, *J. of Biological Chemistry*, 267(31), 22506–11 (1992). Apparently, such cells produce IL-8 only when stressed, and not under conditions of normal growth and homeostasis,. Factors which induce IL-8 production include inflammation, IL-1, TNF, LPS and thrombin.

It is also known that Il-8 is commonly secreted by tumor cells. Tumor is herein defined to mean uncontrolled and progressive multiplication of cells, including benign tumors and all forms of neoplasm and cancer. In one study IL-8 was shown to be present in 80% of carcinoma cell lines and 83.3% of cancer tissues studied. It has also been shown that IL-8 is a growth factor for cancers, and that anti-IL-8 antibody and IL-8 receptor anti-sense are each be effective in attenuating cancer cell growth in vitro. Ishoko, T., et al, Supra; Schadendorf, D., et al., IL-8 Produced by Human Malignant Melanoma Cells in Vitro Is an Essential Autocrine Growth Factor, *J. Immunol.*, 151(5), 2667–2674 (1993).

Because of its effects on growth, it is suspected that IL-8 has a significant role in the metastatic spread of melanoma and other cancers. Schadendorf, D., et al., Supra. It has been demonstrated, for example, that IL-8 is directly involved in the mechanism of melanoma metastasis, (Singh, R. K., et al, Ultraviolet B Irradiation Promotes Tumorigenic and Metastatic Properties in Primary Cutaneous Melanoma via Induction of Interleukin 8, *Cancer Res.*, 55, 3669–3674, 1995), as well as lung cancer, (Greenspoon, S. A., et al., The expression of IL-8 during Tumorgenesis and Metastasis in a model of human nonsmall cell lung cancer/SCID mouse chimera, *Clinical Research*, 42, 404A, 1994). IL-8 has also been found to play role in tumor neovascularization, for example, in head and neck squamous cell carcinomas. Cohen R. F., et al, *Arch Otolaryngol. Head Neck Surg.*, 121, 202–209, 1995. Thus, IL-8 plays important role in tumor growth, metastasis and angiogenesis.

IL-8 RECEPTOR

IL-8 is a ligand for cell-membrane IL-8 Receptor, and it is thought that interaction between IL-8 and IL-8 Receptor is required for IL-8 action. Two IL-8 receptor genes have been identified so far, IL-8 Receptor type A and type B. Both genes belong to the so-called seven transmembrane domain, G protein-coupled receptor family. Receptor A has been shown to be activated by IL-8, and receptor B has been shown to be activated by IL-8 as well as other cytokines belonging to C-X-C family including Melanoma Growth Stimulatory Activity (MGSA). Receptor B is said to be remarkable for its "promiscuity," binding with growth regulatory gene(GRO)(also known as melanoma growth stimulatory activity (MGSA)), neutrophil activating peptide-2 (NAP-2), and neutrophil activating peptide-1 (CAP-1), all of which cluster on human chromosome 4q13-q21.

Ahuja, S. K., Molecular Evolution of the Human Interleukin-8 Receptor Gene Cluster, *Nature Genics*, 2, 31–36 (1992); Cerretti, et al., supra. Common effects elicited by IL-8 and MGSA on neutrophils include calcium mobilization, induction of respiratory burst, degranulation of secretory vesicles, and an increase in both GTPase activity and GTP binding.

IL-8 Receptor B has been found not only in neutrophils and other cells of hematopoietic lineage, but also in non-hematopoietic cells. IL-8 Receptor B has been found, for example, in cells responsive to MGSA, tumor necrosis factor and tumor promoters including placenta and kidney cell lines. Mueller, S. G., et al, Melanoma Growth Stimulatory Activity Enhances the Phosphorylation of the Class II Interleukin-8 Receptor in Non-hematopoietic Cells, *J. Biol. Chem.*, 269, 1973–1980 (1994); NF-κB Subunit-Specific Regulation of the Interleukin-8 Promoter, *Mol. & Cell. Bio.*, 13(10) 6137–6146 (1993). The role and function of IL-8 Receptor B present in cancer and other tumor cells is not fully elucidated. There is, however, evidence that activation of IL-8R B (1) is involved in the mechanism of growth regulation of melanoma and tumorigenic fibroblasts; (2) is associated with transformation of lung cells by asbestos, and (3) correlates with metastic potential of melanoma.

cDNAs coding for at least two IL-8 receptors have been isolated and assigned to chromosome 2q35. Morris, S. W., et al., Assignment of the Genes Encoding Human Interleukin-8 Receptor Types 1 and 2 and an Interleukin-8 Receptor Pseudogene to Chromosome 2q 35, *Genomics*, 14, 685–691 (1992); Murphy, P. M., and Tiffany, H. L., Cloning of Complementary DNA Encoding a Functional Huiman Interleukin-8 Receptor, *Science*, 253, 1280–1283 (1991). Two additional IL-8 receptors have also been identified biochemically, and may correspond to the cDNA's previously identified. Moser, et al., Expression of Transcripts for Two Interleukin Receptors in Human Phagocytes, Lymphocytes and Melanoma Cells, *Biochem.*, 294, 285–292 (1993).

Given the growth stimulatory effect of IL-8 on cells responsive to various tumor growth factors, it would be advantageous to provide antisense oligonucleotides which modulate expression of either IL8 or IL-8 Receptor in cancers in vivo. It would be particularly advantageous to provide oligonucleotides which are effective against lung cancer and melanoma because each of these cancers produce their own growth factors.

There are at least two major types of lung cancer, small cell lung carcinoma (SCLC) and non-small cell lung carcinoma (NSCLC). SCLC comprises approximately one-fourth of the cases, expresses neuroendocrine markers, and generally metastasizes early to lymph nodes, brain, bones, lung and liver. NSCLC comprises the majority of the remaining lung tumor types, and includes adeno-carcinoma, squamous cell carcinoma, and large cell carcinoma. NSCLC is characterized by epithelial-like growth factors and receptors, and is locally invasive.

Melanoma cells, unlike normal melanocytes, can proliferate in the absence of exogenous growth factors. This independence apparently reflects the production of growth factor and cytokines kines for autocrine growth stimulation, including TGF-Å, TGF-Æ, platelet-derived growth factor A and B chains, basic fibroblast growth factor, IL-8, IL-6, IL-1, granulocyte macrophage colony stimulating factor, and MGSA. Guo Y, et al., Inhibition of Human Melanoma Growth and Metastasis in Vivo by Anti-CD44 Monolclonal Antibody. *Cancer Res.*, 54, 1561–1565 (1994).

To date some success has been reported in antisense oligonucleotides at a 20 öM concentration to reduce the expression of IL-8 Receptor and inhibit the growth of lung cancer cells (Ishiko, T., et al, Supra), and malignant melanoma cells (Schadendorf, D., et al, Supra). These reports, however, reflected in vitro studies, and it is not at all clear that the same oligonucleotides would be effective in vivo. Even with respect to in vitro work, at least one researcher reported success only with modified phosphorothioate antisense oligonucleotides. Bargou, R. C., Regulation of Proliferation In The New Hodgkin Cel Line HD-MYZ by Antisense-Oligonucleotides Against IL-6 and IL-8, *Molecular Basis of Cancer Therapy*, edited by E. J. Freidreich, S. A. Stass (1995) Cambridge, Mass., by Blackwell Science Inc. Thus, there is still a need for oligonucleotides which inhibit the growth, metastasis and/or angiogenesis of melanoma and lung cancer in vivo through interferene with the expression of IL-8 and/or IL-8 Receptor. Moreover, since Il-8 and IL-Receptors appear to be involved generally in the mechanisms of tumor growth, metastasis and angiogenesis, phenomena which are characteristic of most types of cancer, there is a need to target one or genes in treating cancers and other tumors in general.

III. SUMMARY OF THE INVENTION

Oligonucleotides are provided which are effective in treatment of tumors, particularly melanoma, lung, prostate and breast cancer. Methods are also provided for use of these oligonucleotides in the treatment of diseases.

IV. BRIEF DESCRIPTION OF THE DRAWINGS

The novel features believed characteristic of the invention are set forth and differentiated in the appended claims. The invention in accordance with preferred and exemplary embodiments, together with further advantages thereof, is more particularly described in the following detailed description taken in conjunction with the accompanying drawing in which:

FIG. 1 is a bar graph showing growth-inhibitory effect of control Oligonucleotide ICN 131, IL-8 Oligonucleotide ICN-70 (SEQ ID NO:2) and IL-8 Oligonucleotide ICN-133 (SEQ ID NO:3) at concentration 0.1 µM on melanoma cells (ATCC HTB140), lung carcinoma (ATCC HTB 177), prostate cancer (ATCC HTB81) and breast cancer cells (T47D) during 72 hrs of treatment. The oligonucleotide designations are as follows:

```
ICN-131    CAC CCG AAG GAA CC         (SEQ ID NO:1)
ICN-70     GAA AGT TTG TGC CTT ATG GA (SEQ ID NO:2)
ICN-133    GGC GCA GTG TGG TCC        (SEQ ID NO:3)
```

FIG. 2 is a bar graph showing the growth-inhibitory effect of IL-Receptor B Oligonucleotide ICN-247 (SEQ ID NO:5), ICN-107 (SEQ ID NO:4) and ICN-297 (SEQ ID NO:6) at concentration 0.1 µM on melanoma cell (ATCC HTB140), non-small lung carcinoma(ATCC HTB177), prostate carcinoma (ATCC HTB81), and breast cancer cells (T47D) during 72 hrs treatment. The oligonucleotide designations are as follows:

```
ICN-107    CTT CCT GTC TGA TGG CTT CT (SEQ ID NO:4)
ICN-247    TGA AAA TTT AGA TCA TC     (SEQ ID NO:5)
ICN-297    AGT GTG CGT GTG G          (SEQ ID NO:6)
```

FIG. 3 is a table showing the kinetic of subcutaneous melanoma growth in balb/c nude/nude mice expressed as slope following linear regression analysis for untreated mice, and mice treated with ICN 131 and ICN-70 (SEQ ID NO:2).

FIG. 4 is a table showing the kinetic of subcutaneous lung cancer growth in balb/c nude/nude mice expressed as slope following linear regression analysis for untreated mice, and mice treated with ICN 131 and ICN-70 (SEQ ID NO:2).

V. DETAILED DESCRIPTION OF SPECIFIC EMBODIMENTS

Synthesis of Oligonucleotides

The discussion below describes the production of various oligonucleotide sequences, and the testing of the sequences for their effectiveness against lung and/or melanoma cancer cells. All tested sequences were synthesized on an automated DNA synthesizer (Applied Biosystems model 394) as phosphodiester oligonucleotides using standard phosphodiester chemistry. The resulting oligonucleotides were purified by HPLC using a reverse phase semiprep C8 column (ABI) with linear gradient of 5% acetonitrile in 0.1 M triethylammonium acetate and acetonitrile. The purity of the products was checked by HPLC using an analytical C18 column (Beckman).

In Vitro Testing

Figure 1:
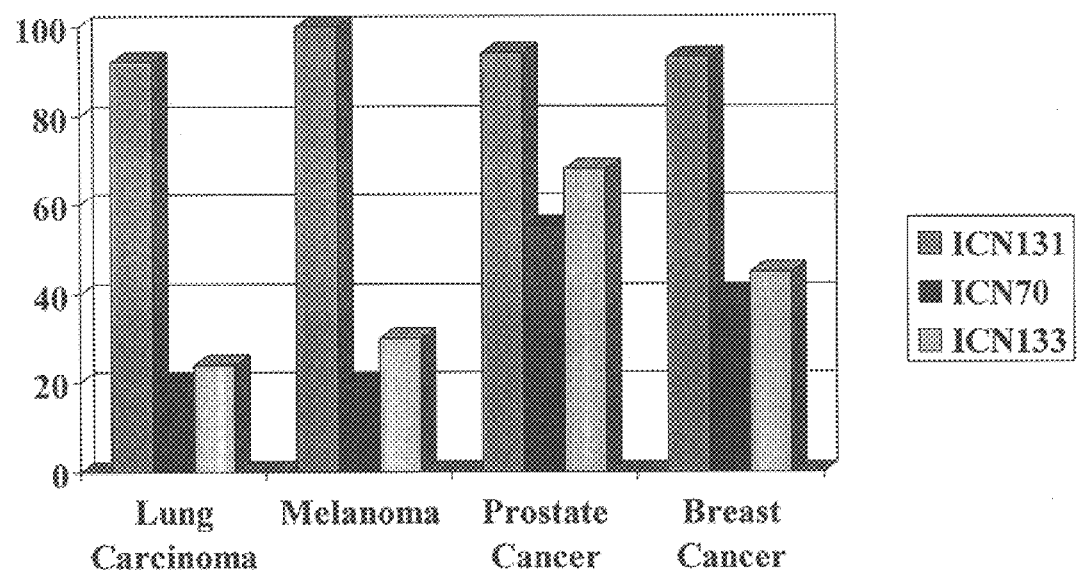
Figure 2:
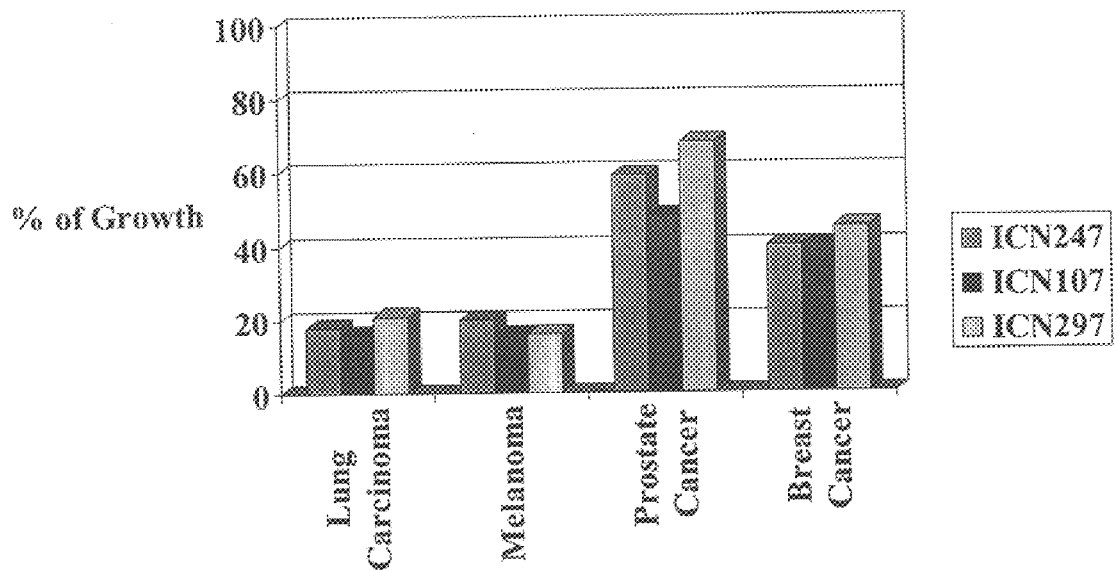

Testing of the oligonucleotide sequences was carried out on large cell lung carcinoma line ATCC HTB 177, melanoma cancer cells ATCC HTB 140, prostate cancer ATCC HTB81 and breast cancer cells T47D. The cells were routinely propagated in culture in a humidified incubator at 37° C. in 5% $CO_2$/ 95% air at atmospheric pressure. Both cell lines were grown as adherent cultures in 90% RPMI 1640, supplemented with 10% fetal bovine serum. Cells were seeded in 96-well microtiter plates at 2,000 cells per well, and subsequently treated once with 0.1 µM concentration of the antisense or control oligonucleotides. After 72 h of culture, all cells were pulsed with 1 µCi/well/200 µl of [$^3$H] thymidine, cultured for an additional 2 h, harvested with an automatic Harvester 96 (Tomtec), and [$^3$H] thymidine incorporation determined in a β-counter. To assure accuracy of the results, all cultures were performed in triplicate and repeated at least three times. The results are presented at FIG. 1 and FIG. 2

In Vivo Testing

The in vivo experiments summarized in FIGS. 3 and 4 were carried out in Balb/c Nude/Nude mice deficient in T lymphocytes but not deficient in B lymphocytes or NK cells. According to the protocol, 2.5 million of melanoma cells (ATCC HBT140) were injected subcutanously in Hanks-balanced salt solution. 10 days later tumor size was measured, and the same day oligonucleotides were injected intratumoraly at a concentration 0.1 $\mu$M in 100 $\mu$L of Hanks-balanced salt Solution. Injection was repeated twice a day for 14 days. Tumor size $mm^2$ was measured 7, 10, and 14 days of treatment. At last day of treatment (day 14) animals were sacrificed for collection of tumor tissues and for their analysis on the histopathological level and gene/protein expression level. In case of lung cancer cells, 0.25 million of the cells were injected (ATCC HBT 177). Subsequently, animals were treated as described for melanoma.

Pharmaceutical Preparations of Oligonucleotides

As with other oligonucleotides, the oligonucleotides of the present invention may be adapted for administration to the body in a number of ways suitable for the selected method of administration, including orally, intravenously, intramuscularly, intraperitoneally, topically, and the like. In addition to comprising one or more different oligonucleotides, the subject pharmaceutical formulations may comprise one or more non-biologically active compounds, i.e., excipients, such as stabilizers (to promote long term storage), emulsifiers, binding agents, thickening agents, salts, preservatives, and the like.

Delivery of oligonucleotides as described herein is well known in the art for a wide range of animals, including mammals, and especially including humans. For example, *Delivery Strategies for Antisense Oligonucleotide Therapeutics*, CRC press (Saghir Akhtar, ed. 1995) details man)y such delivery routes and strategies, and is incorporated herein by reference in its entirety. By way of example only, and without limiting the applicability of the entire book, chapter describes administration by traditional intravenous, intraperitoneal and subcutaneous routes, along with "non-damaging routes" such as intranasal, ocular, transdermal and iontophoresis routes (Id. at 71–83), all of which are applicable to the present invention. Chapter 6 of the same text deals with modifications to make oligonucleotide therapeutics, nuclease resistant, and the terms nucleotide(s), oligonucleotide(s) and nucleic acid base(s) as used herein specifically includes the described modifications and all other conservatively modified variants of the natural form of such compounds. (Id. at 85–104). The claimed oligonucleotides can also be bonded to a lipid or other compound that is actively transported across a cell membrane, either with or without a linker, and administered orally as disclosed in U.S. Pat. No. 5,411,947, which is also incorporated herein by reference. Still further, the oligonucleotides of the present invention can be administered in a "naked" form, encapsulated, in association with vesicles, liposomes, beads, microspheres, as conjugates, and as an aerosol directly to the lung, using for example ICN Biomedicals product no. SPAG 2. Thus, oligonucleotides of the present invention can be administered substantially by all known routes of administration for oligonucleotides, using all accepted modifications to produce nucleotide analogs and prodrugs, and including all appropriate binders and excipients, dosage forms and treatment regimens.

Oligonucleotides can be employed in dosages and amounts which are conventional in the art for the underlying bio-active compound, but adjusted for more efficient absorption, transport and cellular uptake. The dosages may be administered all at once, or may be divided into a number of smaller doses which are then administered at varying intervals of time. At present the most preferred administration of the oligonucleotides of the present invention comprises intravenous administration of between about 0.1 and 100 mg of oligonucleotide per kg of body weight of the patient, 1–14 times per week for approximately 40 days. This regimen is based upon the observed half-life for similar oligonucleotides in vivo of several minutes to several hours, along with the observation that the effect upon protein synthesis may last up to 48 or 72 hours. The specific treatment regimen given to any individual patient will, of course, depend upon the experience of the clinician in weighing the disease involved, the health and responsiveness of the patient, side effects, and many other factors as is well known among such clinicians. For example, greater of lesser dosage levels, and treatment regimens covering greater or lesser periods of time would be dependent upon the judgment of the attending clinician, and may include periods of rest during which treatment with the oligonucleotide is temporarily halted. Treatment may also be combined with other anticancer and palliative treatments as appropriate. Progression/remission of the disease being treated may be determined by following tumor size, extent of metastasis and other factors through radiological analysis and other means known in the art, and the existence and extent of side effects may be determined by following functioning of the liver and/or kidneys, and by following the blood circulation as for example through the use of EKG, which again are well known in the art.

Oligonucleotides may be administered in any convenient manner, such as by oral, intravenous, intraperitoneal, intramuscular, or subcutaneous or other known routes. However, for many of these routes, modified oligonucleotides, including backbone and/or sugar modified nucleotides as set forth in U.S. patent application Ser. No. 08/333,895 and 08/333,545, respectively, the disclosures of which are incorporated herein by reference, may be used advantageously to enhance survivability of the oligonucleotides. For oral administration, oligonucleotides may be administered with an inert diluent or with an assimilable edible carrier, or oligonucleotides may be incorporated directly with the food of the diet. Orally administered oligonucleotides may be incorporates with excipients and used in the form of ingestible tablets, buccal tablets, troches, capsules, elixirs, suspension syrups, wafers, and the like.

The tablets, troches, pills, capsules and the like may also contain the following: a binder, such as gum tragacanth, acacia, cornstarch, or gelatin; excipients, such as dicalcium phosphate; a disintegrating agent such as corn starch, potato starch, alginic acid and the like; a lubricant such as magnesium stearate; and a sweetening agents, such as sucrose, lactose or saccharin; a flavoring agent such as peppermint, oil of wintergreen, or cherry flavoring. When the dosage unit is a capsule, it may contain, in addition to materials of the above type, a liquid carrier. Various other materials may also be present as coatings or to otherwise modify the physical form of the dosage unit. For instance, tablets, pills, or capsules may be coated with shellac, sugar or both. A syrup or elixir may contain sucrose as a sweetening agent, methyl and propylparabens as preservatives, a dye and flavoring such as cherry or range flavor. Such additional materials should be substantially non-toxic in the amounts employed. Furthermore, the oligonucleotides may be incorporated into sustained-release preparations and formulations.

Formulations for parenteral administration may include sterile aqueous solutions or dispersions, and sterile powders for the extemporaneous preparation of sterile, injectable solutions or dispersions. The solutions or dispersions may also contain buffers, diluents, and other suitable additives, and may be designed to promote the cellular uptake of the oligonucleotides in the composition, e.g., the oligonucleotides may be encapsulated in suitable liposomes. Preferably the solutions and dispersions for parenteral administration are sterile and sufficiently fluid for proper administration, sufficiently stable from manufacture and use, and preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by maintenance of the required particle size in the case of dispersion and by the use of surfactants.

Sterile injectable solutions are prepared by incorporating the active compounds in the required amount in the appropriate solvent with one or more of the various other ingredients described above, followed by sterilization. Dispersions may generally be prepared by incorporating the various sterilized active ingredients into a sterile vehicle which contains the basic dispersion medium and the required other ingredients from those listed above. In the case of sterile powders used to prepare sterile injectable solutions, the preferred methods of preparation are vacuum-drying and freeze-drying techniques which yield a powder of the active ingredient plus any additional desired ingredient from previously sterile-filtered solutions.

Pharmaceutical formulations for topical administration may be especially useful with certain bio-active compounds for localized treatment. Formulations for topical treatment included ointments, sprays, gels, suspensions, lotions, creams, and the like. Formulations for topical administration may include, in addition to the subject oligonucleotides, known carrier materials such as isopropanol, glycerol, paraffin, stearyl alcohol, polyethylene glycol, etc. The pharmaceutically acceptable carrier may also include a known chemical absorption promoter. Examples of absorption promoters are e.g., dimethylacetamide (U.S. Pat. No. 3,472,931), trichloro-ethanol or trifluoroethanol (U.S. Pat. No. 3,891,757), certain alcohols and mixtures thereof (British Patent No. 1,001,949), and British patent specification No. 1,464,975.

Solutions of the oligonucleotides may be stored and/or administered as free base or pharmacologically acceptable salts, and may advantageously be prepared in water suitably mixed with a surfactant such as hydroxypropylcellulose. Dispersions can also be prepares in glycerol, liquid polyethylene glycols, and mixtures thereof and in oils. These compositions and preparations may advantageously contain a preservative to prevent the growth of microorganisms.

The prevention of the action of microorganisms can be brought about by various antibacterial and antifungal agents, for example, parabens, chlorobutanol, phenol, sorbic acid, thmerosal, and the like. In many cases, it will be preferable to include isotonic agents such as sodium chloride. Prolonged of injectable compositions can be brought about by the use of agents which delay absorption, such as aluminum monostearate and gelatin.

The compositions and preparations described preferably contain at least 0.1% of active oligonucleotide. The percentage of the compositions and preparations may, of course, be varied, and may contain between about 2% and 60% of the weight of the amount administered. The amount of active compounds in such therapeutically useful compositions and preparations is such that a suitable dosage will be obtained.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the therapeutic active ingredients, its use in the therapeutic compositions and preparations is contemplated. Supplementary active ingredients can also be incorporated into the compositions and preparations.

In addition to the therapeutic uses of the subject oligonucleotides, the oligonucleotides may also be used in the laboratory tool for the study of absorption, distribution, cellular uptake, and efficacy.

INCORPORATION BY REFERENCE

All patents, patents applications, and publications cited are incorporated herein by reference.

EQUIVALENTS

Thus, antisense oligonucleotides effective in controlling IL-8 Receptor expression in non-small cell lung cancer and melanoma cells, have been disclosed. Procedures for using these oligonucleotides in clinical practice have also been disclosed. While specific embodiments and applications have been shown and described, it would be apparent to those skilled in the art that additional modifications are possible without departing from the inventive concepts herein. The invention, therefore, is not to be restricted except in the spirit of the appended claims.

What is claimed is:

1. A method for treating a cancer which is at least partially mediated by IL-8 Receptor, said method comprising the step of administering to a patient an effective amount of the following oligonucleotide: 5' CTT CCT GTC TGA TGG CTT CT 3' (SEQ ID NO: 4).

2. A method for treating a cancer which is at least partially mediated by IL-8, said method comprising the step of administering to a patient an effective amount of an oligonucleotide having the sequence 5' GAA AGT TTG TGC CTT ATG GA 3' (SEQ ID NO:2).

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 14 base pairs
      (B) TYPE: nucleic acid
      (C) STRANDEDNESS: unknown
      (D) TOPOLOGY: unknown (ii) MOLECULE TYPE: DNA (genomic)

(xi) SEQUENCE DESCRIPTION: SEQ ID NO:1:

CACCGGAAGG AACC                                                14

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:2:

GAAAGTTTGT GCCTTATGGA                                          20

(2) INFORMATION FOR SEQ ID NO:3:

(i) SEQUENCE CHARACTERISTICS:
        (A) LENGTH: 15 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:3:

GGCGCAGTGT GGTCC                                               15

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:4:

CTTCCTGTCT GATGGCTTCT                                          20

(2) INFORMATION FOR SEQ ID NO:5:

(i) SEQUENCE CHARACTERISTICS:
        (A) LENGTH: 17 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:5:

TGAAAATTTA GATCATC                                             17

(2) INFORMATION FOR SEQ ID NO:6:

(i) SEQUENCE CHARACTERISTICS:
        (A) LENGTH: 13 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:6:

AGTGTGCGTG TGG                                                 13